United States Patent [19]

Mason et al.

[11] Patent Number: 5,290,557
[45] Date of Patent: Mar. 1, 1994

[54] SAPONIN CONTAINING ANTI-FEEDANT AND MOLLUSCICIDE FOR TERRESTRIAL MOLLUSC CONTROL

[75] Inventors: Wenda M. A. Mason; George S. Puritch, both of Saanichton; David S. Almond, Victoria, all of Canada

[73] Assignee: W. Neudorff GmbH KG, Emmerthal, Fed. Rep. of Germany

[21] Appl. No.: 915,066

[22] Filed: Jul. 16, 1992

[51] Int. Cl.⁵ .................. A01N 25/12; A01N 65/00
[52] U.S. Cl. ................... 424/410; 424/405; 424/500; 424/502; 424/195.1
[58] Field of Search ............. 424/405, 410, 499, 500, 424/502, 195.1; 517/770

[56] References Cited

U.S. PATENT DOCUMENTS 3,956,491  5/1976  Isaac ........................... 424/271

FOREIGN PATENT DOCUMENTS 1277417  6/1968  United Kingdom .

OTHER PUBLICATIONS

Kenneth E. Mott, "Plant Molluscicides", Wiley Medical Publication, presented at meeting for Research and Training in Tropical Diseases held in Geneva Switzerland Jan. 31–Feb. 2, 1983.
Kurt Hostettmann, "Plant-Derived Molluscicides of Current Importance", Economic and Medicinal Plant Research, vol. 3, Copyright 1989, 73–101.
Kurt Hostettmann, "Saponins With Molluscicidal Activity from Hedera" helix L., Helvetica Chimica Acta-vol. 63, Fase. 3 (1980)–Nr. 60.
Dora Godan, "Pest Slugs and Snails Biology and Control", Translated by Shelia Gruber, Springer-Verlag, Berlin, Heidelber, New York 1983 (pp. 236–237).
Lawrence S. Ritchie, et al. "Disinfection and Vector Control", (U.S. Army Trop. Res. Med. Lab., Fort Brooke, Puerto Rico), Milit Med. 128(8): 795–798, Illus. 1963, (Abstract Only).

*Primary Examiner*—Thurman K. Page
*Assistant Examiner*—Neil Levy
*Attorney, Agent, or Firm*—Lahive & Cockfield

[57] ABSTRACT

A composition is provided which serves as an antifeedant, preventing terrestrial molluscs from feeding upon living plants. The active ingredient, which may be present at concentrations of above 0.05% by weight, is a saponin-containing plant extract. At concentrations above about 0.15% by weight, the composition acts as a terrestrial molluscicide. Exemplary sources of the active ingredient include *Yucca schidigera* and *Hedera helix*. The composition may be a liquid or a dry powder, and various formulation enhancing agents may be added to the composition.

5 Claims, No Drawings

SAPONIN CONTAINING ANTI-FEEDANT AND MOLLUSCICIDE FOR TERRESTRIAL MOLLUSC CONTROL

BACKGROUND OF THE INVENTION

The invention relates to effective and environmentally compatible compositions that prevent terrestrial molluscs from feeding on plant tissue.

Terrestrial pulmonate gastropod molluscs, slugs and snails (collectively, "molluscs") are significant crop pests that affect commercial agriculture and horticulture, and domestic gardening. Control of these pests can be achieved through physical trapping, hand picking, physical or chemical barriers, or with chemical controls. Poison baits such as metaldehyde or methiocarb are synthetic chemicals that are effective in poisoning slugs, but snails have developed resistance to some of these pesticides. An additional disadvantage of using such synthetic pesticides is the potential hazard to children and pets should they consume or contact the poison baits.

Certain aquatic molluscs, including snails of the genera Biomphalaria, Bulinus and Oncomelania, have been implicated in the transmission of schistosomiasis, a parasitic disease endemic throughout South America, Africa, and the Far East. These molluscs that live in stagnant or slow moving water serve as vectors for the schistosomes that cause human infection. Schistosomiasis and the organisms responsible for the disease have attracted the attention of many researchers since over 200 million people are affected by the disease.

Although various anti-schistosomal drugs are known, researchers have also sought means to destroy the aquatic mollusc vector. Accordingly, certain naturally occurring compounds have been widely studied and identified as being compounds effective to kill the aquatic molluscs when added to the aquatic environment in which the molluscs live. Among such effective compounds are triterpenoid saponins and spirostanol saponins. These compounds can be extracted from many plants native to the areas affected by schistosomiasis. These plants include the desert palm (*Balanites aegyptiaca*), the sisal plant (*Agave sisalana*), and the cashew tree (*Anacardium occidentale*.L).

Despite the great deal of attention directed to the control of aquatic molluscs using saponin-containing materials, no investigation is known to previously have been made to use these compounds to control terrestrial molluscs. This is so despite the significant problems posed by terrestrial molluscs as crop pests.

Sapogenins are present in several monocot families (e.g., Liliaceae, Amarylidaceae, and Dioscoreaceae) and in dicots (e.g., Scrophulariaceae and Solanoceae). In plants, the sapogenins are combined with sugars to form saponins. The sapogenin may be a steroid or a triterpene, and the sugar moiety may be glucose, galactose, a pentose or a methyl pentose.

Saponins also are widely used in the beverage industry as a foaming agent. In addition, plant extracts containing saponins have been used to enhance microbial growth in septic fields, for reducing ammonia and hydrogen sulfide odors and sludge accumulation in manure holding ponds and lagoons, to control ammonia emissions in floor-raised poultry, and in a variety of other uses. Steroid saponins are also known to be effective in improving crop yields when growing conditions are less than ideal, usually due to drought conditions. The addition of steroid saponins to irrigation water serves to substantially increase crop yields while lowering water demands. In addition, steroid saponins show promise as animal feed additives where they apparently optimize the conditions for microorganisms living in the digestive tract of the animal.

The efficient and safe control of terrestrial molluscs would be of great benefit to agriculture and horticulture. Currently used non-chemical control means are not entirely effective, and quite often can be tedious to use. Currently used chemical control means for terrestrial molluscs rely upon the use of synthetic chemicals that can pose significant dangers to humans, pets, and to the environment. Accordingly, there is a need for a safe, chemically based means that prevent and control the infestation of living plants by terrestrial molluscs.

Thus, it is an object of the invention to provide a method for preventing terrestrial molluscs from feeding upon living plants. A further object of the invention is to provide a safe and effective composition, composed of natural, biodegradable active ingredients, which may be applied to living plants to serve as a terrestrial mollusc antifeedant. Another object of the invention is to provide a safe, effective and biodegradable composition that is fatally toxic to terrestrial molluscs. Other objects of the invention will be apparent upon reading the following disclosure.

SUMMARY OF THE INVENTION

The present invention relates to a safe and effective antifeedant composition that protects living plants from infestation and feeding by terrestrial molluscs. The composition includes a naturally occurring, biodegradable active ingredient that comprises a saponin-containing extract of a plant, such as *Yucca schidigera*. The extract is present at a concentration of at least about 0.01% by weight of the composition and is effective to prevent terrestrial molluscs from feeding on a living plant. At concentrations above about 0.15 wt. %, the composition can be used as a molluscicidal agent.

The saponin-containing extract can be prepared in a liquid or dry form. Liquid extracts maybe used in liquid formulations, with an aqueous carrier, or they may be used in dry formulations with the liquid extract being absorbed into a solid carrier such as a clay or a diatomaceous earth. Dry extracts may be used in dry formulations and applied on or around plants. Alternatively, dry extracts can be used in liquid formulations by dispersing the extract in an oil-based carrier, such as a mineral or vegetable oil.

In addition to the extract and the carrier, liquid formulations may also include one or more gum or gum-like materials that serve as a suspending agent and assist the saponins in remaining adhered to plant surfaces. Liquid formulations may also include an antifreezing additive, an antifoaming agent, and an antioxidant. Solid formulations may use the saponin-containing extract alone, or with other additives. Solid formulations can also include a solid carrier, a dispersant, and a preservative.

The composition is preferably an antifeedant that can be applied directly to plants to prevent feeding on the plants (and the resulting plant damage) by terrestrial molluscs. The composition may also be applied in the vicinity of plants to prevent terrestrial molluscs from infesting a given area. Further, the composition, when used in concentrations of saponin-containing extract above about 0.15 wt. %, may be used as a molluscicidal agent that is fatally toxic to terrestrial molluscs. The molluscicidal embodiment of the composition can be applied on or around plants, or in other areas where mollusc infestation is to be prevented.

As used herein, the term "terrestrial mollusc" refers to various genera and species of non-amphibious and non-aquatic molluscs, snails and slugs. Also, the word "molluscicide" is used to refer to a composition that is effective to kill terrestrial molluscs.

DETAILED DESCRIPTION OF THE INVENTION

The invention comprises a composition that may be applied to living plants to serve as a molluscicide, effective against terrestrial molluscs, and/or as an antifeedant that prevents terrestrial molluscs from feeding upon living plant tissue. The composition may be in liquid form, or it may be a powder able to be dissolved or dispersed in a liquid carrier. Alternatively, the composition may be used in powdered form.

The composition is effective against terrestrial pulmonate gastropod molluscs, slugs and snails, collectively referred to as "terrestrial molluscs." Terrestrial molluscs include agricultural and horticultural pests from the genera Ariolimax. Arion, Boettgerilla, Derocera, Limax, Helix, Lehamannia, Prophysaon, Mariaella, Vaginulus, Parmarion, Milax, Veronicella, Cepaea, Oxychilas, Radix, Bradybaena, Subulina, Xestina, Theba, and Opeas.

The composition comprises as an active ingredient a saponin-containing plant extract which is present at a concentration of at least about 0.01% by weight of the composition and which is effective to repel terrestrial molluscs and to prevent them from feeding on a living plant. The active ingredient preferably is present at concentrations of 3 to 10% by weight as a repellant. Where the composition is intended to be molluscicidal, the active ingredient should be present at a concentration of at least about 0.15% by weight.

Preferably, the composition also includes various formulation enhancing additives. Thus, the composition may also comprise a gum or gum-like material which assists the extract to adhere to plant tissue, an antifreezing composition, a preservative, and an antifoaming agent. Optionally, the composition may include one or more antioxidants and/or UV protectors. Water resisting agents may also be included to enhance the rain fastness of the composition.

The active ingredient is a saponin-containing plant extract which is effective at concentrations at or above 0.01% by weight to prevent terrestrial molluscs from feeding on plant tissue to which the composition has been applied. Saponins are present in many monocot families (e.g., Liliaceae, Amarylidaceae, and Dioscroeaceae) and in dicots (e.g., Scrophulariaceae, Leguminosae, and Solanaceae). Saponins can be extracted from various parts of saponin-containing trees and plants, including the fruit, leaves, roots, bark and trunk. Saponin-containing extracts can be obtained by crushing or pressing suitable portions of the tree or plant to yield a saponin-containing liquid. The liquid may subsequently be purified to remove debris. A saponin-containing extract may also be obtained though solvent extraction using solvents such as methanol, ethanol, acetone, ethyl acetate, chloroform, hexane, and dichloromethane. Further, leaves, bark and other portions of saponin-containing materials may be ground and dried to obtain a suitable solid extract.

One preferred source of saponin-containing extract is the tree *Yucca schidigera*. The extract can be obtained by crushing or pressing the log of the Yucca tree to yield a liquid, and subsequently purifying the liquid to remove debris. Exemplary *Yucca schidigera* extracts are commercially available from Berghausen Corporation, Cincinnati, Ohio as "Yucca Extract 61", and from Calgene Chemical Inc. of Des Plains, Ill. as "AGRO Y-100".

The commercially available Yucca extracts are liquids having a pH in the range of about 3.7 to 4.2. *Yucca schidigera* extracts contain about 45 to 50 percent carbohydrates, of which a variable proportion occurs in the form of both steroidal and triterpenoid saponins, and may include as many as 8 to 10 different saponins. The extract contains numerous saponins. The principal saponin is, however, sarsaponin, which on hydrolysis yields a sarsasapogenin, glucose and galactose. The saponin component of the extract is believed to be the agent which is toxic to the terrestrial molluscs.

Saponin-containing extracts effective as terrestrial mollusc antifeedants or as terrestrial molluscicides are also available from numerous other plant sources. Exemplary plant sources include *Chenopodium ambrosioides* (wormseed), *Chenopodium quinoa*, *Phytolacca dodeandra* (endod), *Swartzia madagascariensis*, and *Hedera helix*.

Saponins are sapogenin glycosides and comprise an aglucan moiety and a sugar moiety. The sapogenin may be a steroid or a triterpene, and the sugar may be a glucose, galactose, pentose, or methyl pentose. The saponin-containing extract active ingredient preferably is present in an antifeedant composition at a concentration range of about 0.01 to 20% by weight of a composition. In compositions intended to be molluscicidal the active ingredient should be present at about 0.15% by weight.

Like most secondary plant compounds, the concentration of saponins within a given plant will vary depending upon the identity of the plant, the source of saponins within the plant (e.g., seed, fruit, leaves), and the conditions under which the plant is grown. The method of saponin extraction will also affect the concentration. Generally, however, saponins are believed to be present in these extracts at about 15 to 25 percent by weight, and typically about 20% by weight.

As noted, the saponin-containing plant extract may be in solid or liquid form. Solid extracts may be applied alone directly to plant surfaces or to other areas where terrestrial mollusc infestation is to be prevented. Solid extracts may also be formulated with various solid additives including preservatives, carriers, dispersants, wetting agents, and sticking agents. Solid formulations are typically in powder form with particle sizes in the range of 1 to 25 $\mu$m.

Carriers and dispersants which can be used with solid antifeedant and molluscicidal compositions include clays (e.g., bentonite clays, kaolinite clays, diatomaceous earths, silica, lignosulfonates, and sodium salts of naphthalene formaldehyde condensates). Carriers and dispersants typically comprise about 25 to 95% by weight of a solid formulation.

Preservatives useful with solid antifeedant and molluscicidal compositions of this invention include 1-(3-chlorallyl)-3,5,7-triaza-1-azoniaadamantane chloride, 5-chloro-2-methyl-4-isothiazolin-3-one, chloroacetamide, and sodium benzoate. Examples of suitable commercially available preservatives include CA-24 (Biochema Schwaben) and Dowicil 200 (Dow Chemical), both of which are solids. The preservatives are preferably present in a solid formulation at about 0.02 to 0.30 wt. %.

Solid saponin-containing extracts may also be used in a liquid antifeedant or molluscicide by dissolving or dispersing the extract in a suitable liquid carrier, such as a mineral or vegetable oil.

Liquid saponin-containing extracts typically are used in liquid formulations with aqueous carriers. Alternatively, however, liquid extracts may be used in solid formulations in which they are absorbed by solid carriers such as clays or diatomaceous earths.

Liquid antifeedant and molluscicidal compositions may include only the extract, but preferably include an aqueous carrier and other formulation improving additives.

Preferred additives include a gum or gum-like component to assist the active ingredient to remain adhered to the plant, an antifreezing composition, a preservative, an antioxidant, water resisting agents to improve rain fastness, and an antifoaming agent to improve processability of the composition.

The gum component may include gums such as guar gum, xanthan gum, cellulose-based materials, elemi tree gum and acacia gum. Additional gum-like materials and binders which may be used include acrylic copolymer, bentonite clay, kaolinite clay, and magnesium aluminum silicate. Gels such as gelatin, hydroxypropyl methylcellulose, and agar may be used as well. A single gum or gum-like material may be used, or various mixtures of these materials may be used. The gums typically are used in the composition in the range of 0.01 to 5% by weight, preferably at about 0.1 to 1.0% by weight.

Among the most preferred gums and gum-like materials are xanthan gum, acacia gum, gelatin, and hydroxypropyl methylcellulose. An example of a suitable acacia gum is Gum Arabic, available from Al-Don Chem. Inc. Exemplary xanthan gums include Kelzan S (Kelco, Co.) and Rhodopol 23 (R. T. Vanderbilt Company). An exemplary HPMC is Methocel K4M (Dow Chemical), and an example of a commercially available gelatin is 300-bloom gelatin (Sigma Chemical).

In one embodiment it is useful to include within liquid compositions anti-freezing agents such as propylene glycol, ethylene glycol, glycerol, and isopropyl alcohol. These additives may be used in concentrations ranging from 1 to 25% by weight and preferably at about 2 to 15% by weight.

Preferred liquid compositions also include a preservative such as those described above. Exemplary commercially available preservatives include Dowcil 200 (cis isomer of 1-(3-chloroally)-3,5,7-triaza-1-azoniaadamantane chloride), Legend MK (5-chloro-2-methyl-4-isothiazolin-3-one) and CA-24. Typically, the preservative is present in the composition at about 0.1 to 1% by weight, and most preferably at 0.1 to 0.3% by weight.

Antioxidants and UV protectors may also be added to the composition at 0.02 to 0.4% by weight. Exemplary antioxidants include butylated hydroxy toluene, ascorbic acid, and tocopherols. UV protectors include PABA, derivatives of PABA, and octyl methoxycinnamate.

In one embodiment it may be useful to include within the composition resins or other waterproofing agents at concentrations of 0.05 to 10% by weight, to enhance the rain fastness of the active ingredient to the plant or other surface to which it is applied. These compounds may be particularly useful in situations where relatively large amounts of rainfall and/or irrigation are expected. Exemplary resins and waterproofing agents which can be used are acrylic copolymer, xanthan gum, and acacia gum.

One property of saponin containing plant extracts is the promotion of foaming in water. Therefore, it is often desirable to include within both solid and liquid molluscicidal and antifeedant compositions an antifoaming agent in order to improve processing of the composition. Typically, the antifoaming/defoaming agent is present at the concentration range of about 0.01 to 1% by weight, and most preferably at about 0.05 to 0.1% by weight. Exemplary antifoaming/defoaming agents are commercially available and include FG-10 (a polydimethylsiloxane) available from Dow Corning Corporation, Midland, Mich. Variations of this material may also be used, such as in the form of silicones, fatty acid esters in hydrocarbons, oleyl alcohols, tallow soap, polypropylene glycol, and tetramethyldecynediol.

Liquid antifeedant and molluscicidal formulations, as previously noted, preferably contain the saponin-containing extract as an active ingredient at concentrations above about 0.1% by weight. Preferably the active ingredient extract is present at concentrations ranging from about 3 to 10% by weight.

As noted above, the composition of the invention may be applied to plants as a liquid, or as a dry powder. A liquid composition may be applied directly to plant tissue by spraying, or by other means, to wet the plant until runoff. The active ingredient should remain adhered to the plant tissue in sufficient concentration to serve as an antifeedant and/or molluscicide for terrestrial molluscs. The composition need not be applied to plant surfaces, but may be applied to non-plant surfaces as well to serve as a barrier and/or trap for terrestrial molluscs. The composition when used in powdered form may be applied to moist plant surfaces to provide a light, even coat of powder. The dry formulation may also be used on non-plant surfaces, to serve as a trap and/or barrier to prevent the terrestrial molluscs from coming in contact with plants.

The invention is further described by the exemplary formulations identified below.

TABLE 1

Exemeplary Concentrateed Liquid Formulations

| Component | Formulation (% By Wt.) | | | | | |
|---|---|---|---|---|---|---|
| | 1-A | 1-B | 1-C | 1-D | 1-E | 1-F |
| Yucca Extract | 50 | 50 | 50 | 50 | 50 | 50 |
| Glycerol | 25 | — | 25 | — | — | 15 |
| Propylene Glycol | — | 25 | — | — | 15 | — |
| Acacia Gum | 0.5 | — | 2 | — | 2 | 2 |
| Xanthan Gum | — | 0.5 | — | — | — | — |
| Antifoam FG-10 | 0.5 | 0.5 | 0.5 | 0.5 | 0.5 | 0.5 |
| Dowicil 200 | 0.1 | 0.1 | 0.1 | 0.1 | 0.1 | 0.1 |
| Water | 23.9 | 23.9 | 22.4 | 49.4 | 32.4 | 32.4 |

Numerous additional concentrated formulations are also possible. For example an oil based formulation may be formed from yucca extract powder (up to about 50% by wt.), a mineral or vegetable oil (up to about 50% by wt.), and a preservative such as CA-24 (at about 0.02 to 0.4% by wt.). Also, a powder based concentrate may include yucca powder (80–90%), kaolinite clay (2-10%), CA-24 preservative (0.3%), tallow soap defoamer (0.1%), and Kelzan S xanthan gum (0.1%).

The following examples serve to further describe the invention.

TABLE 2

Exemplary Ready-to-Use Liquid Formulations

| Component | 2A | 2B | 2C | 2D | E | 2F | 2G | 2H | 2I | 2J | 2K | 2L |
|---|---|---|---|---|---|---|---|---|---|---|---|---|
| Yucca extract | 5 | 5 | 5 | 5 | 5 | 5 | 5 | 5 | 5 | 5 | 5 | 5 |
| Glycerol | — | — | 2.5 | 2.5 | 2.5 | 2.5 | 2.5 | 2.5 | 2.5 | — | — | — |
| Propylene glycol | — | — | — | — | — | — | — | — | — | 2.5 | 2.5 | 2.5 |
| Acacia gum | — | — | — | — | — | — | 0.2 | 0.5 | 0.2 | — | — | — |
| Xanthan gum | — | — | — | 0.1 | 0.2 | 0.1 | 0.1 | — | — | 0.1 | 0.08 | 0.08 |
| Anti-foam FG-10 | — | 0.05 | 0.05 | 0.05 | 0.05 | 0.05 | 0.05 | 0.05 | 0.05 | 0.05 | 0.05 | 0.05 |
| Dowicil 200 | 0.1 | 0.1 | 0.1 | 0.1 | 0.1 | 0.1 | 0.1 | 0.1 | 0.1 | 0.1 | 0.1 | 0.1 |
| Carboset 514H/XL-19 | — | — | — | — | — | — | — | — | — | — | 0.25 514H | 0.25 XL19 |
| Water | | | | | | TO 100 PERCENT | | | | | | |

The concentrated liquid formulations identified in Table 1 typically are diluted with water before use to achieve an active ingredient concentration in the range of 0.05 to 20% by weight of the concentration. Preferably, the concentration of the yucca extract active ingredient is in the range of 3 to 10% by weight.

Saponins can be derived from other sources in addition to *Yucca schidigera*. For example, the methanol and aqueous extracts of ripe *Hedera helix* berries also yield useful saponin sources.

An exemplary technique for obtaining a methanol extract of such berries is as follows. Approximately 150 g. of methanol is added to 40 g. of the ripe berries and the mixture is blended for about 30 seconds. The mixture is then stirred for about 45 minutes and vacuum filtered to collect the extract.

An aqueous extract can similarly be obtained by adding about 200 g. of distilled water to 40.2 g. of berries, followed by blending for 30 seconds. The mixture is then stirred, while heating to 60° C., for about 30 minutes. The extract can be collected by vacuum filtration.

The Hedera berry extracts can be preformulated by mixing with a spreading agent and diluting with water. Various spreading agents can be used, including fatty acid salts. A suitable commercially available spreading agent is Safer Insecticidal Soap, available from Safer, Inc. The extract may be used in the preformulation at 0.5 to 20% by wt., while the spreading agent is used at 0.1 to 1.0% by wt.

*Hedera helix* extracts may be applied as molluscicidal agents in the form of a preformulation of the type shown in Table 3. Alternatively, the preformulation may be further formulated as described above with respect to the *Yucca schidigera* extracts using antifreezing agents, preservatives, antifoamers, and water proofing agents. The extract may be used directly in formulations of the type described above, without the preparation of preformulations.

TABLE 3

Preformulations of Aqueous and Methanol Extracts of *Hedera helix* Berries

| Component | Preformulation (wt. %) | | |
|---|---|---|---|
| | 3-A | 3-B | 3-C |
| Extract | 1.0 | 10.0 | 20.0 |
| Spreading Agent | 0.2 | 0.2 | 0.2 |
| Water | 99.4 | 89.8 | 79.8 |

EXAMPLE 1

Two centimeters of moist vermiculite were placed in each of ten plastic trays (26×53 cm) and covered with one layer of paper towel. Vaseline coated tape was covered in salt and placed on the edges of the trays to keep the slugs and snails from escaping. The antifeedant/molluscicidal formulations used in this example were prepared in glass beakers using the formulations of Table 2 and corresponding controls from which the active ingredient was deleted. Individual leaves of Romaine lettuce were excised, tagged with labelled tapes on the cut edge, and dipped into the test antifeedant/molluscicidal formulations. Ten leaves were treated with each formulation, drip dried, and one leaf of each treatment was randomly placed in each of the ten trays. Twenty slugs (*Arion hortensis*, *Arion circumscriptus*, *Deroceras sp.*, *Ariolimax sp.*, and *Limax sp.*) and one brown snail were randomly placed within each tray. The condition of the leaves was assessed at 24, 48 and 70 hours post treatment (HPT). The results of the experiment, demonstrating the antifeedant activity of various formulations, based on the percent of leaf eaten, are demonstrated in Table 4.

TABLE 4

(Example 1 Results)

| Formulation | Percent Eaten | | |
|---|---|---|---|
| | 24 HPT | 48 HPT | 70 HPT |
| Formulation 2-A | 0 | 0 | 1 |
| Formulation 2-B | 0 | 5 | 6 |
| Formulation 2-C | 0 | 7 | 15 |
| Formulation 2-D | 4 | 4 | 11 |
| Formulation 2-E | 0 | 4 | 16 |
| Formulation 2-F | 3 | 4 | 17 |
| Formulation 2-G | 0 | 0 | 0 |
| Formulation 2-H | 2 | 2 | 6 |
| Formulation 2-I | 1 | 2 | 18 |
| Control 2-D (no a i) | 41 | 54 | 75 |
| Control 2-E (no a i) | 45 | 85 | 89 |
| Control 2-F (no a i) | 35 | 59 | 69 |
| Control 2-G (no a i) | 32 | 64 | 77 |
| Control 2-H (no a. i.) | 44 | 63 | 72 |
| Control 2-I (no a i) | 49 | 70 | 86 |
| Control 2-C (no a i) | 31 | 47 | 65 |
| Untreated | 57 | 77 | 76 |

EXAMPLE 2

The procedure of Example 1 was followed, however, the tested antifeedant/molluscicidal formulation included only *Yucca schidigera* extract (Berghausen Yucca 61), diluted with water to the stated concentration. An antifoaming agent (Antifoam FG-10) was also added at 0.05% for each formulation. No spreading agents or sticking agents such as gums, were included in the formulations. The results are shown below in Table 5.

TABLE 5

(Example 2 Results)

| Formulation | Percent Eaten | | |
|---|---|---|---|
| | 24 HPT | 48 HPT | 70 HPT |
| 2% Yucca 61 Extract | 7 | 17 | 25 |
| 3% Yucca 61 Extract | 6 | 12 | 17 |
| 4% Yucca 61 Extract | 6 | 13 | 16 |
| 5% Yucca 61 Extract | 3 | 9 | 14 |
| Untreated | 71 | 81 | 87 |

EXAMPLE 3

Four groups each of four french marigolds were transplanted from 15 cm pots into a 1.4 m² field plot. The plot was formed by using a wooden quadrat made of 2 inch by 6 inch boards coated in Vaseline and salt, topped along the edges with aluminum flashing to prevent wash off of the salt during watering and rainfall. Two "houses" were located in the center of the plot for the molluscs. Each house comprised a 15 cm diameter wet clay pot sunk in the ground. Stakes around the perimeter of the pot raised a clay saucer 2 cm above the pot to provide a cool, moist refuge for the molluscs. The following day, the antifeedant formulations were applied as a spray and allowed to dry for several hours. Five *Arion ater*, five large Ariolimax and two small Ariolimax were equally divided between the two houses and closed in for several hours before lifting the saucers to allow the molluscs free range. Twenty-one days later four Delphiniums were transplanted from 15 cm pots into the quadrat, locating each plant alternately between the remaining marigold plants. The same day, the marigold plants were watered overhead with 1 cm of water and the Group 2 marigolds were retreated with antifeedant formulation. The Groups 1, 3 and 4 marigolds were left untreated. The marigolds and delphiniums were treated by spraying according to the treatments outlined below in Table 6. Rainfall, irrigation and temperature were recorded for the duration of the experiment. Mollusc feeding on the plants was recorded at least every other day. One additional *Limax sp.* slug entered the plot and took up residence early in the experiment. The results recorded during the experiment are shown in Tables 7 and 8.

TABLE 6

(Example 3 Treatments)

| Group | Marigolds Formulation/Retreatment | Delphiniums Formulation/Treatment* |
|---|---|---|
| 1 | 2J/No | Untreated |
| 2 | 2J/Yes (as necessary for 34 days) | 1C/leaves, lower stem |
| 3 | 2B/No | 1C/leaves, stem, flowers |
| 4 | Untreated | 1D/leaves only |

*Concentrated Formulations diluted before application to 5% a. i., plant areas treated are noted.

TABLE 7

(Example 3 Results - Marigolds)

| Group | Formulation | Days After Treatment (% Eaten) | | | | | | |
|---|---|---|---|---|---|---|---|---|
| | | 7 | 20 | 25 | 32 | 34 | 37 | 43 |
| 1. | 2J | 5 | 10 | 10 | 5 | 30 | 80 | 80 |
| 2. | 2J* | 0 | 0 | 5 | 15 | 20 | 80 | 90 |
| 3. | 2B | 0 | 20 | 35 | 60 | 80 | 80 | 95 |
| 4. | Untreated | 25 | 95 | 95 | 95 | 95 | 95 | 99 |
| Rain + Irrigation (Cumulative Total-cm) | | 0.09 | 0.34 | 1.34 | 1.36 | 3.28 | 8.02 | 8.04 |

*Resprayed at 22 DAT and 29 DAT.

TABLE 8

(Example 3 Results - Delphiniums)

| Group | Formulation | Days After Treatment/ Treatment Area (% Eaten) | | | |
|---|---|---|---|---|---|
| | | 12 Overall | 12 Flower and Seed Pods | 20 Overall | 20 Flower and Seed pods |
| 1 | untreated | 15 | 15 | 70 | 90 |
| 2 | 1C | 5 | 0* | 10 | 90 |
| 3 | 1C | 5 | 0* | 10 | 0 |
| 4 | 1D | 5 | 0* | 10 | 0 |

Total Rainfall over period was 6.74 cm.
*Denotes Feeding on lower leaves only.

EXAMPLE 4

A plot of lettuce seedlings was established and surrounded by a 1 m² 2"×4" wooden quadrat treated with Vaseline and salt to prevent escape by the molluscs. A wet clay pot was sunk in the center of the pot, with a clay saucer supported over the pot as a shelter for the slugs. The quadrat was divided into four treatment areas and sprayed twelve days after planting as follows. The first treatment area was treated with a formulation 1C, diluted to 5% a.i., and applied daily. The second treated area was sprayed with formulation 1C, diluted to 5% a.i., and applied three times weekly. The third treatment area was sprayed with formulation 1C, diluted to 10% a.i., applied three times weekly. The fourth treatment area was left untreated. The molluscs (four *Arion ater*, one Ariolimax, and three *Limax sp.*) were added to the plot after the first spray application. The results of this experiment are illustrated in Table 9.

TABLE 9

(Example 4 Results)

| Group | Formulation & Application | Days After Treatment (% Eaten) | | | | |
|---|---|---|---|---|---|---|
| | | 7 | 10 | 12 | 14 | 16 |
| 1 | Form. 1C - Daily* | 0 | 0 | 0 | 0 | 35 |
| 2 | 1C - 3 × per week | 0 | 0 | 0 | 25 | 60 |
| 3 | 1C - 3 × per week, 10% ai | 0 | 0 | 0 | 15 | 20 |
| 4 | Untreated | 5 | 35 | 50 | 75 | 95 |
| Rain & Irrigation Cum. Total (cm) | | 0.09 | 1.09 | 2.09 | 2.29 | 4.2 |

*Treatment 1 did not receive retreatment on day 15 due to rain.

EXAMPLE 5

Formulation 1C was prepared and diluted as indicated in Table 10. 5 ml of each diluted treatment was used to wet filter paper which lined the top and bottom of separate petri dishes. Cucumber cubes were place in each dish, and one each of *Deroceras sp* and *Arion circumscriptus*, were added to the petri dishes. The mean survival of each of the two molluscs was assessed at 27 and 64 hours post treatment (HPT), and the data is illustrated in Table 10.

TABLE 10

(Example 5 Results)

| | Treatments | Mean Survival (/2) | |
|---|---|---|---|
| | | 27 HPT | 64 HPT |
| 1 | Water | 2 | 2 |
| 2 | 0.16% a i | 1 | 0 |
| 3 | 0.31% a i | 0 | 0 |
| 4 | 0.63% a i | 0 | 0 |
| 5 | 1.25% a i | 0 | 0 |
| 6 | 2.50% a i | 0 | 0 |

EXAMPLE 6

Cos lettuce var. Parris Island were grown in a greenhouse to the first stage in 2.25 cm² pots (21 days post planting). Ripe *Hedera helix* berries, extracted in methanol, were prepared in the manner desribed above. The resulting supernatant weighed 180.5 g. Preformulations were prepared as described in Table 3. In addition, preformulations 3A and 3B were mixed with Yucca extract formulations. Ten replicates of lettuce were sprayed to runoff with the solutions using a trigger sprayer, and allowed to dry. The plants were placed on their sides with wet vermiculite and covered with a paper towel. Ten full grown *Arion ater* slugs were added to the trays. A ventilated plastic lid was placed on top of each tray. The plants were assessed two days after the addition of the slugs to the trays and the data is shown in Table 11.

TABLE 11

(Example 6 Results)

| | Treatment | % Eaten & DMRT[1] | | |
|---|---|---|---|---|
| 1 | Untreated | 57 | A | |
| 2 | 5% a i Form. 1-B | 24 | | C |
| 3 | 0.01% MeOH extract | 50 | A B | |
| 4 | 0.05% MeOH extract | 23 | | C |
| 5 | 0.10% MeOH extract | 24 | | C |
| 6 | 0.01% Aqueous extract | 33 | B | C |
| 7 | 0.05% Aqueous extract | 35 | B | C |
| 8 | 0.10% Aqueous extract | 33 | B | C |

TABLE 11-continued (Example 6 Results)

| | Treatment | % Eaten & DMRT[1] | |
|---|---|---|---|
| 9 | No. 3 + No. 2 | 24 | C |
| 10 | No. 5 + No. 2 | 24 | C |

[1]Means not followed by the same letter are considered significantly different using Duncan's Multiple Range Test at $p < 0.05$.

It is understood that various modifications may be made to the invention described herein without departing from the intended scope of the invention.

What is claimed is:

1. A composition suitable for application to living plants to protect living plants from feeding by terrestrial molluscs, consisting essentially of:

a saponin-containing extract of *Yucca schidigera* or *Hedera helix*, in naturally occurring form, effective to prevent terrestrial molluscs from feeding on the plant and present at a concentration range of about 0.03 to 20% by weight of the composition;

a gum or gum-like material selected from the group consisting of acacia gum, xanthan gum, gelatin, and hydroxypropyl methyl cellulose, present at a concentration range of about 0.01% to 1.0% by wt.;

an antifreezing component selected from the group consisting of glycerol, propylene glycol, ethylene glycol, and isopropyl alcohol, present at a concentration range of about 1 to 25% by wt.; and a liquid carrier selected from the group consisting of water, mineral oil and vegetable oil.

2. The composition of claim 1 wherein the saponin-containing extract and the gum are solids, dissolved in a liquid carrier.

3. The composition of claim 1 wherein the saponin-containing extract, the gum component and the antifreezing component are all in the liquid phase.

4. The composition of claim 1, further consisting of an antioxidant selected from the group consisting of butylated hydroxy toluene, ascorbic acid, and tocopherols, present at 0.02 to 0.4% by wt.

5. The composition of claim 4 further consisting of water-resisting agent selected from the group consisting of acrylic copolymer, xanthan gum, and acacia gum, serving to improve the rain fastness of the composition, and being present at a concentration range of about 0.05 to 10% by wt.

* * * * *